United States Patent [19]

Chan

[11] Patent Number: 5,256,785
[45] Date of Patent: Oct. 26, 1993

[54] SMOKING COMPOSITIONS CONTAINING AN OXALATE FLAVORANT-RELEASE ADDITIVE

[75] Inventor: W. Geoffrey Chan, Chesterfield, Va.

[73] Assignees: Philip Morris Incorporated, New York, N.Y.; Philip Morris Products Inc., Richmond, Va.

[21] Appl. No.: 942,394

[22] Filed: Sep. 9, 1992

Related U.S. Application Data

[62] Division of Ser. No. 822,695, Jan. 21, 1992, Pat. No. 5,172,706.

[51] Int. Cl.$^5$ .................. C07D 241/12; C07D 403/12; C07D 213/55
[52] U.S. Cl. ................... 544/336; 544/357; 546/193; 131/278
[58] Field of Search ................ 544/336, 357

[56] References Cited

U.S. PATENT DOCUMENTS 4,620,004  10/1986  Sanders et al. ............. 544/357
5,080,719  1/1992  Houminer et al. ............ 546/348

*Primary Examiner*—Emily Bernhardt
*Attorney, Agent, or Firm*—James E. Schardt

[57] ABSTRACT

In one embodiment this invention provides smoking compositions which contain a novel oxalate ester flavorant-release additive.

Under cigarette smoking conditions, a combustible filler additive such as methyl 2-pyrazinyl-2-propanyl oxalate or di(2-pyrazinyl-2-propanyl) oxalate pyrolyzes and releases 2-isopropenylpyrazine flavorant as a volatile component of the cigarette smoke.

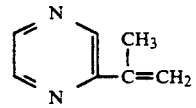

6 Claims, No Drawings

SMOKING COMPOSITIONS CONTAINING AN OXALATE FLAVORANT-RELEASE ADDITIVE

This application is a division of application Ser. No. 07/822,695, filed Jan. 21, 1992, now U.S. Pat. No. 5,172,706.

BACKGROUND OF THE INVENTION

It has been established that alkylpyrazines are natural components of tobacco smoke, and that they are contributors to tobacco smoke flavor [A. Baggett et al J. Chromatog. 97, 79 (1974)] 2-Isopropenylpyrazine has been identified as a tobacco flavorant constituent of burley tobacco [E. Demole et al, Helv. Chem. Acta, 55, 1866 (1972)].

Patents which disclose the addition of various pyrazine compounds to tobacco and foodstuffs as a means of providing flavor or flavor enhancement include U.S. Pat. Nos. 3,684,809; 3,705,158; 3,754,934; 3,764,349; 3,767,426; and 881,025.

Alkylpyridines also have been found to be useful tobacco additives. U.S. Pat. No. 3,625,224 describes the use of methylpyridines, ethylpyridines and various dialkylpyridines as tobacco additives. U.S. Pat. No. 3,381,691 discloses 2-methyl-5-isopropylpyridine as a tobacco additive.

It is characteristic of pyrazine and pyridine and other heteroaromatic derivatives employed as tobacco flavorants in the prior art that the respective derivatives have the disadvantage of both high volatility and low odor threshold. Both of these properties significantly restrict the extent that these heteroaromatic derivatives can be utilized as flavorants in tobacco compositions. A quantity of a pyrazine or pyridine derivative in a tobacco composition sufficient to have a noticeable effect in low delivery cigarettes causes a marked pack aroma.

U.S. Pat. No. 4,259,969 endeavors to overcome some of the disadvantages of the above-described flavorant technology. The patent describes smoking composition flavorant-release additives such as 2,3-dihydroxy-2,3-dimethyl-1,4-bis(3,5,6-trimethyl-2-pyrazinyl)butane. Under smoking conditions substitute pyrolysis products are released which enhance the flavor of the mainstream smoke and improve the aroma of the sidestream smoke.

U.S. Pat. No. 4,312,368 and related U.S. Pat. No. 4,479,003 describe heterocyclic-hydroxy-substituted alkanoate flavorant additives such as ethyl 2-(2-butyl)-3-hydroxy-3-methyl-3-(3-pyridyl)propionate, which under normal smoking conditions pyrolyzes into components which contribute enhanced flavor and aroma to the smoke streams. U.S. Pat. No. 4,872,918 describes heteroaromatic ester flavorant-release additives such as methyl 3,5,6-trimethyl-2-pyrazineacetate, which is adapted to release tetramethylpyrazine flavorant under cigarette smoking conditions.

There is continuing research effort to develop improved smoking compositions which contain a new and efficient low volatility flavorant-release additive, and which generate mainstream smoke with flavorant-enhanced taste and character under smoking conditions.

Accordingly, it is an object of this invention to provide smoking compositions having incorporated therein a flavorant component which is characterized by lack of mobility and/or volatility at ambient temperature.

It is another object of this invention to provide smoking compositions having incorporated therein a flavorant-release additive which under normal smoking conditions yields pyrolysis constituents which impart improved flavor to mainstream smoke and improved aroma to sidestream smoke.

It is another object of this invention to provide novel oxalate compounds of low volatility which are adapted to be incorporated into cigarette fillers, and which under normal smoking conditions release a volatile heteroaromatic flavorant constituent into cigarette smoke.

It is a further object of this invention to provide a novel process for producing substituted heteroaromatic compounds Other objects and advantages of the present invention shall become apparent from the following description and examples.

DESCRIPTION OF THE INVENTION

One or more objects of the present invention are accomplished by the provision of a smoking composition comprising an admixture of (1) combustible filler selected from natural tobacco, reconstituted tobacco and tobacco substitutes, and (2) between about 0.0001-5 weight percent, based on the total weight of filler, of a flavorant-release additive corresponding to the formula:

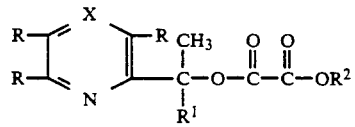

where X is nitrogen or carbon; R is hydrogen or a $C_1-C_4$ alkyl substituent; $R^1$ is a $C_1-C_4$ alkyl substituent; and $R^2$ is a $C_1-C_8$ alkyl substituent.

In another embodiment this invention provides a smoking composition comprising an admixture of (1) combustible filler selected from natural tobacco, reconstituted tobacco and tobacco substitutes, and (2) between about 0.0001-5 weight percent, base on the total weight of filler, of a flavorant-release additive corresponding to the formula:

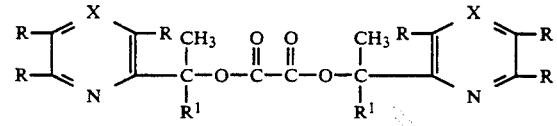

where X is nitrogen or carbon; R is hydrogen or a $C_1-C_4$ alkyl substituent; and $R^1$ is a $C_1-C_4$ alkyl substituent.

Illustrative of $C_1-C_4$ and $C_1-C_8$ alkyl groups are methyl ethyl, propyl, 2-propyl, butyl, 2-butyl, isobutyl, pentyl, hexyl 2-hexyl, heptyl, octyl, and the like.

In another embodiment this invention provides novel oxalate esters corresponding to the formula:

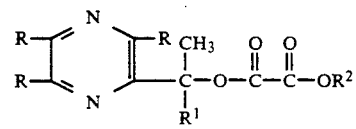

I where R is hydrogen or a $C_1$-$C_4$ alkyl substituent; R is a $C_1$-$C_4$ alkyl substituent; and $R^2$ is a $C_1$-$C_8$ alkyl substituent.

In another embodiment this invention provides novel oxalate esters corresponding to the formula:

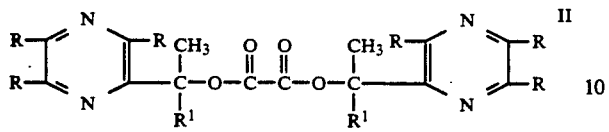

where R is hydrogen or a $C_1$-$C_4$ alkyl substituent; and $R^1$ is a $C_1$-$C_4$ alkyl substituent.

An invention oxalate ester compound as described above when incorporated in a smoking composition, is a low volatility additive which under normal smoking conditions pyrolyzes and releases a volatile heteroaromatic constituent which enhances the flavor and aroma of low delivery cigarette smoke.

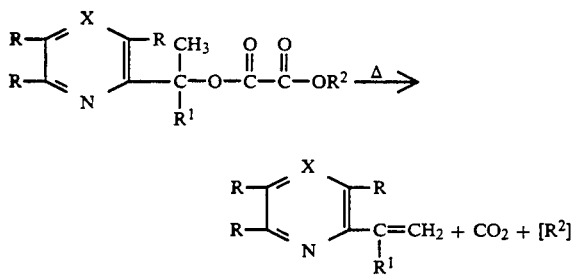

The present invention oxalate esters are stable and odorless compounds at ambient temperature. In addition, the oxalate esters decompose at a relatively low pyrolysis temperature (e.g., 130°-300° C.) to release a heteroaromatic product in essentially quantitative yield.

A present invention oxalate ester also has utility as starting material for the production of an isopropenyl-heteroaromatic compound. This is accomplished by subjecting a present invention oxalate ester corresponding to Formula I or Formula II to thermolysis conditions at a temperature between about 130°-300° C. for a period between about 0.1-0.5 hour until the reaction is completed. A yield of at least about 95 percent of theoretical is obtained.

Preparation of Oxalate Ester Compounds

One method of synthesizing the invention oxalate ester compounds is by the reaction of an acetylpyrazine or acetylpyridine compound with alkyllithium to form an alcohol intermediate, and then reacting the alcohol with alkyl oxalyl chloride or oxalyl dichloride:

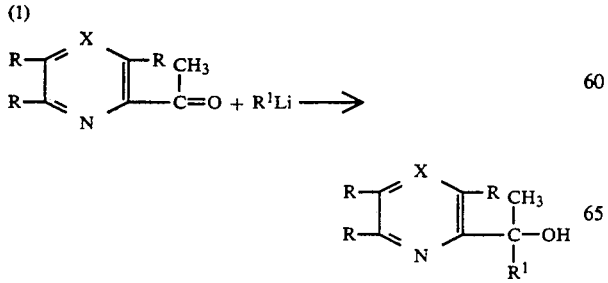

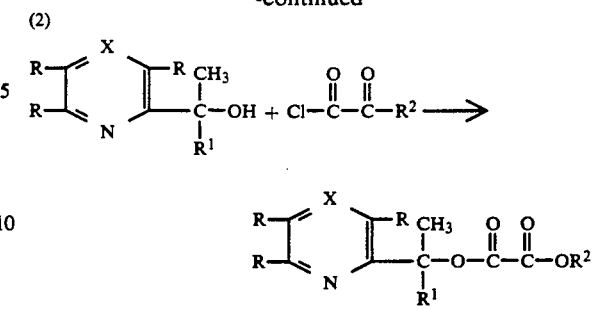

Preparation Of Smoking Compositions

In a further embodiment, this invention provides a method of preparing a smoking composition which is adapted to impart flavor and aroma to mainstream and sidestream smoke under smoking conditions, which method comprises incorporating into natural tobacco, reconstituted tobacco or tobacco substitute between about 0.0001-5 weight percent, based on composition weight, of a flavorant-release additive corresponding to Formula I or Formula II as previously defined above.

The invention flavorant-release additive can be incorporated into the tobacco or tobacco substitute in accordance with methods known and used in the art. Preferably the flavorant-release additive is dissolved in a solvent such as alcohol or aqueous alcohol and then sprayed or injected into the tobacco and/or tobacco substitute matrix. Such method ensures a even distribution of the flavorant additive throughout the filler, and thereby facilitates the production of a more uniform smoking composition. Alternatively, the flavorant may be incorporated as part of a concentrated tobacco extract which is applied to a fibrous tobacco web as in the manufacture of reconstituted tobacco. Another suitable procedure is to incorporate the flavorant in tobacco or tobacco substitute filler in a concentration between about 0.5-5 weight percent, based on the weight of filler, and then subsequently to blend the treated filler with filler which does not contain flavorant additive.

The term "tobacco substitute" is meant to include non-tobacco smoking filler materials such as are disclosed in U.S. Pat. Nos. 3,703,177; 3,796,222; 4,019,521; 4,079,742; and references cited therein; incorporated herein by reference.

An invention flavorant-release additive also can be incorporated in the paper wrapper of cigarette products for the purpose of enhancing the aroma of cigarette sidestream smoke under smoking conditions.

The following Examples are further illustrative of the present invention. The specific ingredients and processing parameters are presented as being typical, and various modifications can be derived in view of the foregoing disclosure within the scope of the invention.

EXAMPLE I

2-Pyrazinyl-2-propanol

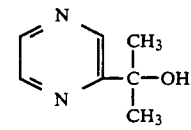

2-Acetylpyrazine (12.2 g, 0.1 mole) was dissolved in tetrahydrofuran (140 mL). 1,10-phenanthrolin was added as an indicator, and the solution was cooled to −30° C. Methyllithium (1.5M in hexane) was added dropwise through an addition funnel over a 30 minute period while maintaining the temperature at < −20° C., and about 60 mL of methyllithium was used to reach a dark colored end point. The mixture was stirred at this temperature for 30 minutes, and then was poured into ice water (200 g). The organic layer was separated and the aqueous layer was extracted with hexane (4×100 mL) and ether (5×100 mL). The combined organic solution was dried with anhydrous MgSO₄. Gas Chromatographic analysis indicates a 47:53 ratio of acetylpyrazine to product.

The solvent was removed by rotary evaporation under aspirator vacuum to provide a light yellow liquid. An analytical pure sample of the 2-pyrazinyl-2-propanol product was isolated by preparative gas chromatography. NMR and IR spectra confirmed the structure of the title compound.

2-Pyridinyl-2-propanol is prepared by using 2-acetylpyridine in place of 2-acetylpyrazine.

EXAMPLE II

Methyl 2-pyrazinyl-2-propanyl oxalate

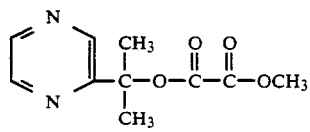

The 2-pyrazinyl-2-propanol and acetylpyrazine mixture of Example I was dissolved in dichloromethane (50 mL), and pyridine (8.4 g, 0.106 mole) and dimethylaminopyridine (1.3 g, 10.6 mmole) were added. The solution was cooled in an ice-acetone bath, and methyl oxalyl chloride (7.8 g, 63.7 mmole) in dichloromethane (10 mL) was added dropwise over a 15 minute period. After addition was completed, GC indicated the presence of acetylpyrazine and the desired product, and the absence of starting alcohol. The solution then was poured into 50 g of ice and stirred vigorously. The resultant organic layer was separated, and the aqueous layer was extracted with dichloromethane (25 mL). The combined organic layer was back extracted with saturated sodium chloride solution (50 mL).

The organic solution was dried over MgSO₄ and filtered, and the solvent was evaporated to provide a light yellow, viscous oil product. The oil was distilled by Kugelrohr distillation under 100 millitorr vacuum at room temperature to remove acetylpyrazine. The pot temperature then was raised to 75° C. to distill the final product as a light yellow liquid, yield 8.5 g. NMR and IR spectra confirmed the structure of the title compound Oxalyl dichloride (30 mmole) is substituted for methyl oxalyl chloride to produce di(2-pyrazinyl-2-propanyl) oxalate.

EXAMPLE III

2-Isopropenylpyrazine

-continued

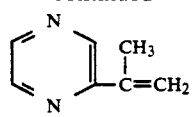

A flash vacuum pyrolysis apparatus was assembled, which consisted of a 2-necked round bottomed flask (equipped with a bleed tube) connected to a glass pyrolysis tube inside a tube furnace oven, and a U-tube. The glass pyrolysis tube was filled with glass beads (5 mm diameter) and was heated to 300° C. by the heating oven. The U-tube was cooled in acetone/dry ice bath and was connected to a vacuum source operating at 100 millitorr vacuum. The round bottomed flask was heated in an oil bath to vaporize the starting material. The bleed tube was used to introduce a slow stream of nitrogen into the system to carry the vapor into the heat zone.

Methyl 2-pyrazinyl-2-propanyl oxalate (1 g, 4.46 mmole) was placed in the round bottomed flask and heated to a temperature of 150° C. After all the starting oxalate was vaporized, 520 mg of product (97% yield) was recovered from the U-tube. NMR and IR spectra confirmed the structure of the title compound.

Similar pyrolysis results are obtained with di(2-pyrazinyl-2-propanyl) oxalate.

EXAMPLE IV 2-(3'-Methylpyrazinyl)-2-propanol

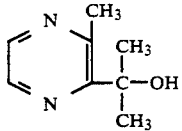

2-Acetyl-3-methylpyrazine (5 g, 36.8 mmole) was dissolved in tetrahydrofuran (40 mL) and the solution was cooled in an acetone/dry ice bath. 1,10-Phenanthroline was added as an indicator, and methyllithium (1.5M in hexane) was added dropwise until a dark colored end point was reached, while the reaction medium temperature was maintained at < −60° C. After addition was completed, GC indicated that only the desired alcohol product was present.

The solution was poured into ice water (50 g) and the mixture was extracted with ethyl ether (3×50 mL). The organic solution was dried with anhydrous MgSO₄ and filtered, and evaporation of the solvent provided a light yellow liquid. Distillation of the liquid with a Kugelrohr apparatus at 1 torr vacuum (bp 61° C.) gave 5.0 g (90% yield) of product. NMR and IR spectra confirmed the structure of the title compound.

2-(3'-methylpyridinyl)-2-propanol is prepared by using 2-acetyl-3-methylpyridine in place of 2-acetyl-3-methylpyrazine.

EXAMPLE V

Methyl 2-(3'-methylpyrazinyl)-2-propanyl oxalate

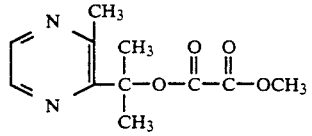

2-(3'-Methylpyrazinyl)-2-propanol (4 g, 26.3 mmole), dimethylaminopyridine (0.3 g, 2.5 mmole) and pyridine (4.2 g, 52.6 mmole) were dissolved in dichloromethane (20 mL). The solution was cooled in an ice/acetone bath (15° C. to −10° C.) and methyl oxalyl chloride (3.9 g, 31.8 mmole) dissolved in dichloromethane (8 mL) was added dropwise over a 15 minute period. GC indicated the absence of alcohol reactant, and there were one large peak for the product and a small peak corresponding to the pyrolyzed product.

The solution was poured into 20 g of ice, and the organic layer was washed with saturated NaHCO₃ solution, and with saturated NaCl solution, and then dried over MgSO₄. After filtration of the solution and evaporation of the solvent, the resultant light yellow liquid was distilled under vacuum with a Kugelrohr apparatus at 85° C. to provide 5.6 g (90% yield) of product. The product was recrystallized from dichloromethane/hexane, and NMR and IR spectra confirmed the structure of the title compound.

Oxalyl dichloride (13 mmole) is substituted for methyl oxalyl chloride to produce di[2-(3'-methylpyrazinyl)-2-propanyl oxalate.

EXAMPLE VI

2-Isopropenyl-3-methylpyrazine

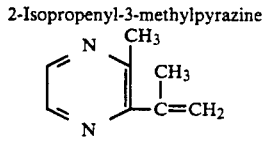

Utilizing a pyrolysis apparatus as described in Example III, methyl 2-(3'-methylpyrazinyl)-2-propanyl oxalate (1 g, 4.2 mmole) was placed in the reactor and heated to a pyrolysis temperature of 150° C. After all of the oxalate reactant was vaporized, 500 mg of product (89% yield) was recovered from the cooled U-tube. NMR and IR spectra confirmed the structure of the title compound.

Similar pyrolysis results are obtained with di[2-(3'-methylpyrazinyl)-2-propanyl oxalate.

EXAMPLE VII

Methyl 2-(3',6'-dimethylpyrazinyl)-2-propanyl oxalate

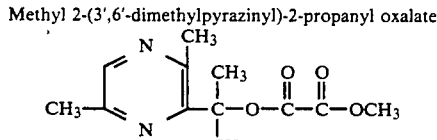

2-Acetyl-3,6-dimethylpyrazine (2 g, 13.3 mmole) was dissolved in tetrahydrofuran (30 mL), and the solution was cooled in an acetone/dry ice bath. 1,10-Phenanthroline was added as an indicator, and methyllithium (1.5M) was added dropwise until a red end point was attained, and the mixture was stirred at −78° C. for an additional 30 minutes.

Methyl oxalyl chloride (3.27 g, 26.7 mmole) in tetrahydrofuran (5 mL) was added slowly to the pyrazine solution and the resulting solution was warmed to room temperature. Ice (20 g) was added to the reaction medium, and saturated NaHCO₃ solution was added until the aqueous solution remained slightly basic. The formed layers were separated and the aqueous solution was extracted with hexane (2×30 mL). The combined organic extracts were washed with water and with saturated NaCl solution. After drying over MgSO₄, the solution was filtered and evaporated to a light yellow oil. A crude product was isolated by preparative HPLC on silica gel using 40% ethyl acetate in hexane as eluent. The product (2.8 g, 83% yield) was recrystallized from ethyl acetate/hexane, and NMR and IR spectra confirmed the structure of the title compound.

A more polar fraction was obtained from the preparative HPLC, and NMR and IR spectra confirmed the structure as 2-(3',6'-dimethylpyrazinyl)-2-propanol.

2-(3',6'-dimethylpyradinyl)-2-propanol is prepared by using 2-acetyl-3,6-dimethylpyridine in place of 2-acetyl-3,6-dimethylpyrazine.

Oxalyl dichloride (13 mmole) is substituted for methyl oxalyl chloride to produce di[2-(3',6'-dimethylpyrazinyl)-2-propanyl] oxalate.

EXAMPLE VIII

2-Isopropenyl-3,6-dimethylpyrazine

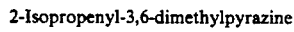
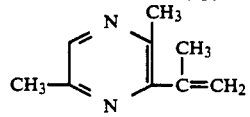

Utilizing a pyrolysis apparatus as described in Example III, methyl 2-(3'-methylpyrazinyl)-2-propanyl oxalate (785 mg, 3.1 mmole) was placed in the reactor and was heated to a pyrolysis temperature of 180° C. After all of the starting oxalate was vaporized, 425 mg of product (92% yield) was recovered from the U-tube. NMR and IR spectra confirmed the structure of the title compound.

Similar pyrolysis results are obtained with di[2-(3',6'-dimethylpyrazinyl)-2-propanyl] oxalate.

EXAMPLE IX

3-Methyl-2-(3',6'-dimethylpyrazinyl)-2-butanol

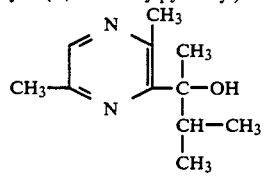

2-Isobutyryl-3,6-dimethylpyrazine (6 g, 33.7 mmole) was dissolved in tetrahydrofuran (100 mL), and the solution was cooled in an acetone/dry ice bath. 1,10-Phenanthroline was added as an indicator, and methyllithium (1.5M in hexane) was added dropwise until a dark colored end point was reached, while the reaction medium temperature was maintained at <−60° C. After addition was completed, GC indicated that only the desired alcohol was present. The solution was poured into ice water (50 g) and the mixture was extracted with ethyl ether (3×50 mL). The organic solution was dried with anhydrous MgSO₄ and filtered, and evaporation of the solvent provided a light yellow liquid. Distillation of the liquid with a Kugelrohr apparatus at 0.1 torr vacuum (bp 42° C.) gave 5.8 g (88% yield) of the product. NMR and IR spectra confirmed the structure of the title compound.

3-Methyl-2-(3',6'-dimethylpyridinyl)-2-butanol is prepared by using 2-isobutyryl-3,6-dimethylpyridine in place of 2-isobutyryl-3,6-dimethylpyrazine.

EXAMPLE X

Methyl 3-methyl-2-(3',6'-dimethylpyrazinyl)-2-butyl oxalate

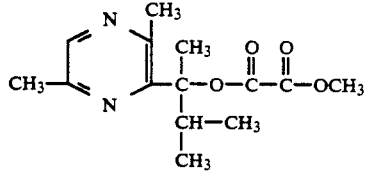

3-Methyl-2-(3',6'-dimethylpyrazinyl)-2-butanol (5 g, 25.8 mmole), dimethylaminopyridine (0.3 g, 2.5 mmole) and pyridine (3.5 g, 44.3 mmole) were dissolve in ethyl acetate (50 mL). The solution was cooled in an ice/acetone bath (−15° C. to −10° C.) and methyl oxalyl chloride (3.8 g, 30.9 mmole) in ethyl acetate (7 mL) was added dropwise over a 15 minute period. After the mixture was stirred at room temperature for 4 hours, HPLC indicated an absence of alcohol reactant, and one large peak for the product.

The solution was poured into 20 g of ice, and the organic layer was separated and washed with saturated $NaHCO_3$ solution, and with saturated NaCl solution, and then dried over $MgSO_4$. After filtration of the solution and evaporation of the solvent, the resultant semi-solid was distilled under vacuum with a Kugelrohr apparatus at 80° C. to give 6.0 g (83% yield) of product. The product was recrystallized from dichloromethane/hexane, and NMR and IR spectra confirmed the structure of the title compound.

Oxalyl dichloride (15 mmole) is substituted for methyl oxalyl chloride to produce di[3-methyl-2-(3',6'-dimethylpyrazinyl)-2-butyl] oxalate.

EXAMPLE XI

3-Methyl-2-(3',6'-dimethylpyrazinyl)-1-butene

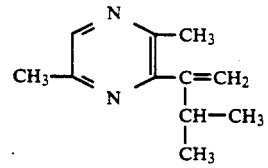

Utilizing a pyrolysis apparatus as described in Example III, methyl 3-methyl-2-(3',6'-dimethylpyrazinyl)-2-butyl oxalate (1 g, 3.57 mmole) was placed in the reactor and was heated to a pyrolysis temperature of 180° C. After all of the starting oxalate was vaporized, 600 mg of product (95% yield) was recovered from the U-tube. NMR and IR spectra confirmed the structure of the title compound.

Similar pyrolysis results are obtained with di[3-methyl-2-(3',6'-dimethylpyrazinyl)-2-butyl] oxalate.

What is claimed is:

1. An oxalate ester corresponding to the formula;

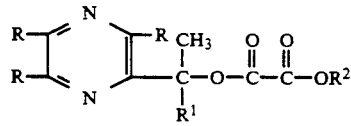

where R is hydrogen or a $C_1$-$C_4$ alkyl substituent; $R^1$ is a $C_1$-$C_4$ alkyl substituent; $R^2$ is a $C_1$-$C_8$ alkyl substituent.

2. An oxalate ester corresponding to the formula:

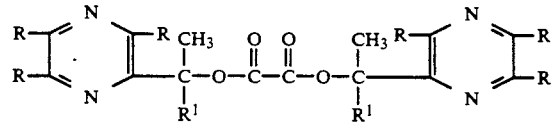

where R is hydrogen or a $C_1$-$C_4$ alkyl substituent; and $R^1$ is a $C_1$-$C_4$ alkyl substituent.

3. Di(2-pyrazinyl-2-propanyl) oxalate.
4. Di[2-(3'methylpyrazinyl)-2-propanyl] oxalate.
5. Di[2-(3',6'-dimethylpyrazinyl)-2-propanyl] oxalate.
6. Di[3-methyl-2-(3',6'-dimethylpyrazinyl)-2-butyl] oxalate.

* * * * *